(12) United States Patent
Piascik et al.

(10) Patent No.: US 8,617,704 B2
(45) Date of Patent: Dec. 31, 2013

(54) SURFACE MODIFICATION FOR ENHANCED SILANATION OF CERAMIC MATERIALS

(75) Inventors: Jeffrey Robert Piascik, Raleigh, NC (US); Jeffrey Yates Thompson, Davie, FL (US); Sonia Grego, Chapel Hill, NC (US); Brian R. Stoner, Chapel Hill, NC (US)

(73) Assignees: Research Triangle Institute, Research Triangle Park, NC (US); Nova Southeastern University, Ft. Lauderdale, FL (US)

( * ) Notice: Subject to any disclaimer, the term of this patent is extended or adjusted under 35 U.S.C. 154(b) by 0 days.

(21) Appl. No.: 13/273,528

(22) Filed: Oct. 14, 2011

(65) Prior Publication Data
US 2012/0034572 A1 Feb. 9, 2012

Related U.S. Application Data (63) Continuation of application No. PCT/US2010/031348, filed on Apr. 16, 2010.

(60) Provisional application No. 61/170,463, filed on Apr. 17, 2009.

(51) Int. Cl.
*B32B 9/04* (2006.01)
*C23C 16/00* (2006.01)
*C23C 16/40* (2006.01)
*B32B 15/04* (2006.01)

(52) U.S. Cl.
USPC .... 428/336; 427/2.26; 427/2.29; 427/255.18; 427/255.37; 427/539; 428/333; 428/448; 428/450; 428/451

(58) Field of Classification Search
USPC ......... 428/333, 336, 448, 450, 451; 427/2.26, 427/2.29, 255.18, 255.37, 539
See application file for complete search history.

(56) References Cited

U.S. PATENT DOCUMENTS 4,364,731 A * 12/1982 Norling et al. ............... 433/218
4,673,354 A * 6/1987 Culler ......................... 433/217.1

(Continued)

FOREIGN PATENT DOCUMENTS

EP 1669477 6/2006

OTHER PUBLICATIONS

Amaral et al., "Microtensile Bond Strength of a Resin Cement to Glass Infiltrated Zirconia-Reinforced Ceramic: The Effect of Surface Conditioning," *Dental Materials*, 2006, pp. 283-290, vol. 22.

(Continued)

*Primary Examiner* — Dhirajlal S. Nakarani
(74) *Attorney, Agent, or Firm* — Womble Carlyle Sandridge & Rice, LLP (57) ABSTRACT

A coated medical implant, such as a coated dental component, is provided, the coated medical implant including a substrate surface formed of a material comprising available hydroxyl groups and a silicon oxide coating layer chemisorbed on the substrate surface. A method for the preparation of such coated implants is also provided, the method involving application of the silicon oxide coating layer to the substrate surface by chemical vapor deposition. A dental structure is also provided, which includes a first dental component having a substrate surface formed of a material comprising available hydroxyl groups; a silicon oxide coating layer chemisorbed on the substrate surface; a silane coupling agent overlying and covalently attached to the silicon oxide layer; a dental cement overlying and coupled to the silane coupling agent; and a second dental component having a surface bonded to the dental cement.

30 Claims, 9 Drawing Sheets

(56) References Cited

U.S. PATENT DOCUMENTS

| | | | |
|---|---|---|---|
| 5,011,410 A | * | 4/1991 | Culler et al. .................. 433/208 |
| 5,827,577 A | | 10/1998 | Spencer |
| 2005/0271810 A1 | | 12/2005 | Kobrin et al. |
| 2005/0271893 A1 | | 12/2005 | Kobrin et al. |
| 2006/0088666 A1 | | 4/2006 | Kobrin et al. |
| 2006/0201425 A1 | | 9/2006 | Kobrin et al. |
| 2006/0213441 A1 | | 9/2006 | Kobrin et al. |
| 2006/0251795 A1 | | 11/2006 | Kobrin et al. |
| 2007/0020392 A1 | | 1/2007 | Kobrin et al. |
| 2008/0081151 A1 | | 4/2008 | Kobrin et al. |
| 2008/0160531 A1 | | 7/2008 | Korlach |
| 2008/0241512 A1 | | 10/2008 | Boris et al. |
| 2008/0248263 A1 | | 10/2008 | Kobrin |
| 2008/0274281 A1 | | 11/2008 | Kobrin et al. |
| 2008/0299288 A1 | | 12/2008 | Kobrin et al. |
| 2008/0312356 A1 | | 12/2008 | Kobrin et al. |

OTHER PUBLICATIONS

Blatz et al., "Resin-Ceramic Bonding: A Review of the Literature", *J. Prosthet. Dent.* 2003, pp. 268-274, vol. 89.

Kern et al., "Bonding to Zirconia Ceramic: Adhesion Methods and their Durability", *Dent. Mat.* 1998, pp. 64-71, vol. 14.

Matinlinna et al., "Silane Based Concepts on Bonding Resin Composite to Metals," *The Journal of Contemporary Dental Practice*, 2007, pp. 1-13, vol. 8, No. 2.

Denry et al. "State of the Art of Zirconia for Dental Applications," *Dental Materials*, 2008, pp. 299-307, vol. 24.

* cited by examiner

SURFACE MODIFICATION FOR ENHANCED SILANATION OF CERAMIC MATERIALS

CROSS-REFERENCE TO RELATED APPLICATIONS

This application is a continuation of international application number PCT/US2010/031348, filed Apr. 16, 2010, which claims priority to U.S. provisional application No. 61/170,463, filed Apr. 17, 2009, both of which are incorporated herein by reference in their entireties and for all purposes.

FEDERALLY SPONSORED RESEARCH OR DEVELOPMENT

This invention was made with United States Government support under DE013511-09, awarded by National Institute of Health (NIH)/National Institute of Dental and Craniofacial Research (NIDCR). The United States Government has certain rights in the invention.

FIELD OF THE INVENTION

The invention is related to methods for affixing medical implants, including dental and orthopedic implants and devices, by functionalizing the surface of the implants or devices. It is also related to medical implants wherein the outer surface may be functionalized to afford reactivity with various other materials.

BACKGROUND OF THE INVENTION

Statistics show that nearly 70% of adults ages 35 to 44 have lost at least one permanent tooth to an accident, gum disease, a failed root canal, or tooth decay. By age 74, it is reported that 26% of adults have lost all of their permanent teeth. Both the increasing aging population and a growing awareness for oral health and aesthetics have led to the growth of dental implant surgery. A dental implant is a permanent post anchored to the jawbone and topped with a prosthetic (implant abutment and synthetic crown or bridge) that can be permanently attached to the post. Single teeth or an entire arch of teeth may be effectively replaced with dental implants and attached prosthetics, which can last for significant periods of time with routine maintenance. Dental implant surgery is now considered to be the fastest growing area in dentistry.

Dental implant posts are typically made of titanium or titanium alloys, which generally are anchored to bone via osseointegration (intimate physical contact between the synthetic implant and the surrounding bone). Traditionally, metallic prosthetic components have been used to restore implants. However, recent commercial development has focused on alternative materials, especially ceramics. Ceramics provide high strength as well as the natural look of real teeth. In many cases, ceramics have higher wear resistance, corrosion resistance, toughness, and strength than metals and metal alloys. In particular, recent research has focused on high strength ceramics such as alumina and zirconia. These materials provide better fracture resistance and long-term durability than traditional porcelain and other ceramics.

The methods for attaching a substrate (natural tissue like tooth structure or implant abutment) to a prosthetic restorative may be micromechanical, or may additionally include chemical bonding through silanation or other surface treatment techniques. In some applications, adhesive bonding is not required and the ceramic material may be placed and affixed using conventional cements that rely on micromechanical retention. Micromechanical retention may be achieved in some cases by merely roughening the surfaces of the substrate or the restorative. However, these conventional cementation techniques do not provide the high bond strength required for some applications. In such applications, good adhesion is often important for high retention, prevention of microleakage, and increased fracture and fatigue resistance, and may be provided by resin-based cements used in conjunction with intermediate adhesion promoters, like dental silanes. Strong resin bonding relies on micromechanical interlocking as well as adhesive chemical bonding to the ceramic surface and requires a combination of surface roughening and chemical functionalization for efficient attachment.

Surface roughening may be achieved by grinding, abrasion with diamond rotary instruments, surface abrasion with alumina particles, acid etching with acids such as hydrofluoric acid (HF), or a combination of these techniques. Adhesive chemical bonding is commonly achieved through a two-step process, which initially involves treating the implant or restorative with a silane coupling agent. The silane coupling agents are organic compounds that contain silicon atoms, are similar to orthoesters in structure, and may display dual reactivity. Silanes typically contain one or more alkoxy groups, wherein the alkoxy groups can react with an inorganic substrate. The other end of the molecule is organically functionalized, for example, with a vinyl, allyl, isocyanate, or amino group, and can polymerize with an organic matrix such as a methacrylate. The next step of achieving the adhesive chemical bonding is using an organic resin-based cement to react with the organically functionalized silane to affix adherends.

This adhesive chemical bonding, which is required for many dental applications, is not applicable to high strength ceramic materials. Because of the composition and physical properties of high-strength ceramics, they are not easily etched or chemically functionalized using conventional treatments. Traditional silane chemistry is not effective with high strength ceramics because such materials are more chemically stable (inert) than silica-containing materials and are not as easily hydrolyzed. Furthermore, due to their hardness and strength, the surfaces of high strength ceramics are not easily roughened. Acid etchants such as HF do not sufficiently roughen the surface. These materials may be roughened only by very aggressive mechanical abrasion methods, which may create fatigue-enhancing surface flaws.

One method that can be used to provide adhesive chemical bonding of high strength ceramics requires surface abrasion with alumina particles coated with silica. The alumina particles impact the surface, transferring a thin silica layer via a tribochemical process, which allows for chemical bonding to a silane coupling agent, which can then bond to a resin-based cement. However, this method is a relatively complicated procedure and does not produce bond strengths as high as those reported for silane-bonded porcelain. In addition, air particle abrasion may be particularly unsuitable for zirconia-based materials, as it is likely to generate micro-fractures which could lead to premature, catastrophic failure.

Alternatively, the use of phosphoric acid primers or phosphate-modified resin cements has been shown to produce silane-like adhesion through similar types of hydrolyzation-driven chemistry. However, the bond strengths reported are generally even lower than those reported for the tribochemical silica coating in combination with silane and resin cement. One recent study has shown increased bond strength using selective infiltration etching and novel silane-based zirconia primers. See Aboushelib M N, Matinlinna J P, Salameh Z, Ounsi H., Innovations in Bonding Zirconia-Based Materials: Part I. *Dent. Mat.* 2008; 24: 1268-1272. However, the available approaches for adhesive bonding of high strength ceramics are not adequate for all clinical applications and their long-term efficacy is currently unknown. A non-destructive, simple method for treating high strength ceramic surfaces would be desirable to render the high strength ceramic surfaces suitable for use with existing adhesive bonding techniques.

BRIEF SUMMARY OF THE INVENTION

One aspect of the present invention provides a medical implant comprising a substrate surface formed of a material comprising available hydroxyl groups and a silicon oxide coating layer chemisorbed on said substrate surface, wherein the silicon oxide layer is deposited by chemical vapor deposition. The medical implant may be, but is not limited to, a dental component selected from the group consisting of dental implants, crowns, bridges, fillings, veneers, inlays, onlays, endodontic devices, and orthodontic brackets.

The material comprising the medical implant may comprise a metal oxide. For example, the material may be, but is not limited to, zirconia, alumina, titania, chromium oxide, or a combination thereof.

In some aspects, the medical implant may be a dental component. The dental component may further comprise a silane coupling agent covalently attached to the silicon oxide layer. In certain aspects, the silane coupling agent may be, but is not limited to, 3-methacryloyloxypropyltrimethoxysilane, (3-trimethoxysilylpropylmethacrylate), 3-acryloyloxypropyltrimethoxysilane, 3-isocyanatopropyltriethoxysilane, N-[3-(trimethoxysilyl)propylethylenediamine], 3-mercaptopropyltrimethoxysilane, bis-[3-(triethoxysilyl)propyl] polysulfide, and combinations thereof. In some aspects, the dental component may further comprise an overlying dental cement coupled to the silane coupling agent. The dental cement may be, but is not limited to, polymer-based adhesives, cements and composites, resin-modified glass ionomers and combinations thereof. The dental cement may be covalently bonded to the silane coupling agent.

In some aspects, the thickness of the silicon oxide layer on the medical implant is less than about 50 nm. In certain aspects, the thickness of the silicon oxide layer on the medical implant is less than about 30 nm. In certain aspects, the thickness is less than about 10 nm. In certain aspects, the thickness of the silicon oxide layer is between about 0.1 nm and about 5 nm.

In another aspect of the invention is provided a dental structure, comprising a first dental component having a substrate surface formed of a material comprising available hydroxyl groups; a silicon oxide coating layer chemisorbed on the substrate surface, wherein the silicon oxide layer is deposited by chemical vapor deposition; a silane coupling agent overlying and covalently attached to the silicon oxide layer; a dental cement overlying and coupled to the silane coupling agent; and a second dental component having a surface bonded to the dental cement. In certain aspects, one of the first and second dental components is selected from the group consisting of dental implants, crowns, bridges, fillings, veneers, inlays, onlays, endodontic devices, and orthodontic brackets. In certain aspects, the surface of the second dental component is constructed of a material that is natural tooth, metal, porcelain fused to metal, porcelain, ceramic, resin, or a combination thereof.

Another aspect of the invention provides a method of preparing the surface of a medical implant for silanation, comprising providing a medical implant comprising a substrate surface formed of a material comprising available hydroxyl groups and applying a silicon oxide coating layer to the substrate surface of the medical implant by chemical vapor deposition. The application step may comprise contacting the surface of the dental component with one or more gaseous silicon-based precursors and water vapor. The silicon-based precursor may be selected from the group consisting of tetrachlorosilane ($SiCl_4$), tetrafluorosilane ($SiF_4$), tetrabromosilane ($SiBr_4$), trichlorosilane ($HSiCl_3$), trifluorosilane ($HSiF_3$), tribromosilane ($HSiBr_3$), hexachlorodisilane ($Si_2Cl_6$), hexachlorodisiloxane ($Si_2Cl_6O$), and combinations thereof. In some aspects, the thickness of the silicon oxide coating layer introduced in the applying step may be less than about 10 nm.

In some aspects, the medical implant is a dental component, and the method further comprises reacting the silicon oxide surface of the dental component with a silane coupling agent. In certain aspects, the silane coupling agent may be, but is not limited to, 3-methacryloyloxypropyltrimethoxysilane, (3-trimethoxysilylpropylmethacrylate), 3-acryloyloxypropyltrimethoxysilane, 3-isocyanatopropyltriethoxysilane, N-[3-(trimethoxysilyl)propylethylenediamine], 3-mercaptopropyltrimethoxysilane, bis-[3-(triethoxysilyl)propyl] polysulfide, and combinations thereof. The silane coupling agent may further be coupled to a dental cement. The dental cement may be, but is not limited to, polymer-based adhesives, cements and composites, resin-modified glass ionomers and combinations thereof. The method may still further comprise bonding the dental component to another substrate with the dental cement.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

One aspect of the invention relates to methods of preparing the surface of a medical implant (which may be a dental or orthopedic implant or device) for silanation by depositing thereon a silicon oxide coating. Coating a medical implant in this way allows the implant to be subsequently silanated such that it can be affixed to a variety of surfaces using conventional cements or resins. Another aspect of the invention relates to the coated medical implants and to the subsequently silanated medical implants. Still another aspect of the invention relates to silanated medical implants further reacted with one or more cements or resins, which can be used to affix the medical implant to a variety of surfaces.

"Medical implant" as used herein means any physical object that can be implanted into the body or which comes in direct contact with the body. Medical implants that may be used according to the methods of the present invention include, but are not limited to, dental components, including dental implants, restoratives, and orthodontic devices, as well as orthopedic devices and implants. Any medical implant that may be affixed to another surface or device by a resin or cement may be coated according to the present invention.

"Dental implant" as used herein means a post (i.e., a dental abutment) anchored to the jawbone and topped with individual replacement teeth or a bridge that is attached to the post or posts. The term is meant to encompass traditional dental implants as well as mini-dental implants. In some cases where the dental abutment is in the form of natural tooth, the dental implant only comprises the implanted replacement tooth or bridge.

"Restorative" as used herein means any dental component used to restore the function, integrity and/or morphology of any missing tooth structure. Examples of restoratives that may be coated according to the methods described herein include, but are not limited to, crowns, bridges, fillings, veneers, inlays and onlays, as well as endodontic devices including endodontic cones and devices for endodontic root perforation repair.

"Orthodontic device" as used herein means any device intended to prevent and/or correct irregularities of the teeth, particularly spacing of the teeth. Orthodontic devices particularly relevant to the present invention include but are not limited to orthodontic brackets.

"Dental component" as used herein encompasses any component of a dental implant or a restorative or an orthodontic device and can even include, in certain embodiments, natural tooth.

"Orthopedic device" or "orthopedic implant" as used herein means a device that replaces a part or function of the body. Orthopedic devices include but are not limited to devices adapted to form artificial joints, including hips, knees, and elbows.

The medical implant can comprise any surface material comprising available hydroxyl groups on its surface. For example, the medical implant may be a metal, which inherently has a metal oxide layer on its surface, a polymer or copolymer, or a metal oxide. In certain embodiments, the metal implant comprises a refractory metal oxide. In one embodiment, the medical implant comprises a zirconia, alumina, titania, or chromium-oxide-based material or a combination thereof. In another embodiment, the medical implant may be a metallic device that is surface passivated with an oxide film. For example, the surface of the metal implant may comprise titanium oxide on a titanium alloy, or chromium oxide on stainless steel or cobalt chrome.

Figure 1:
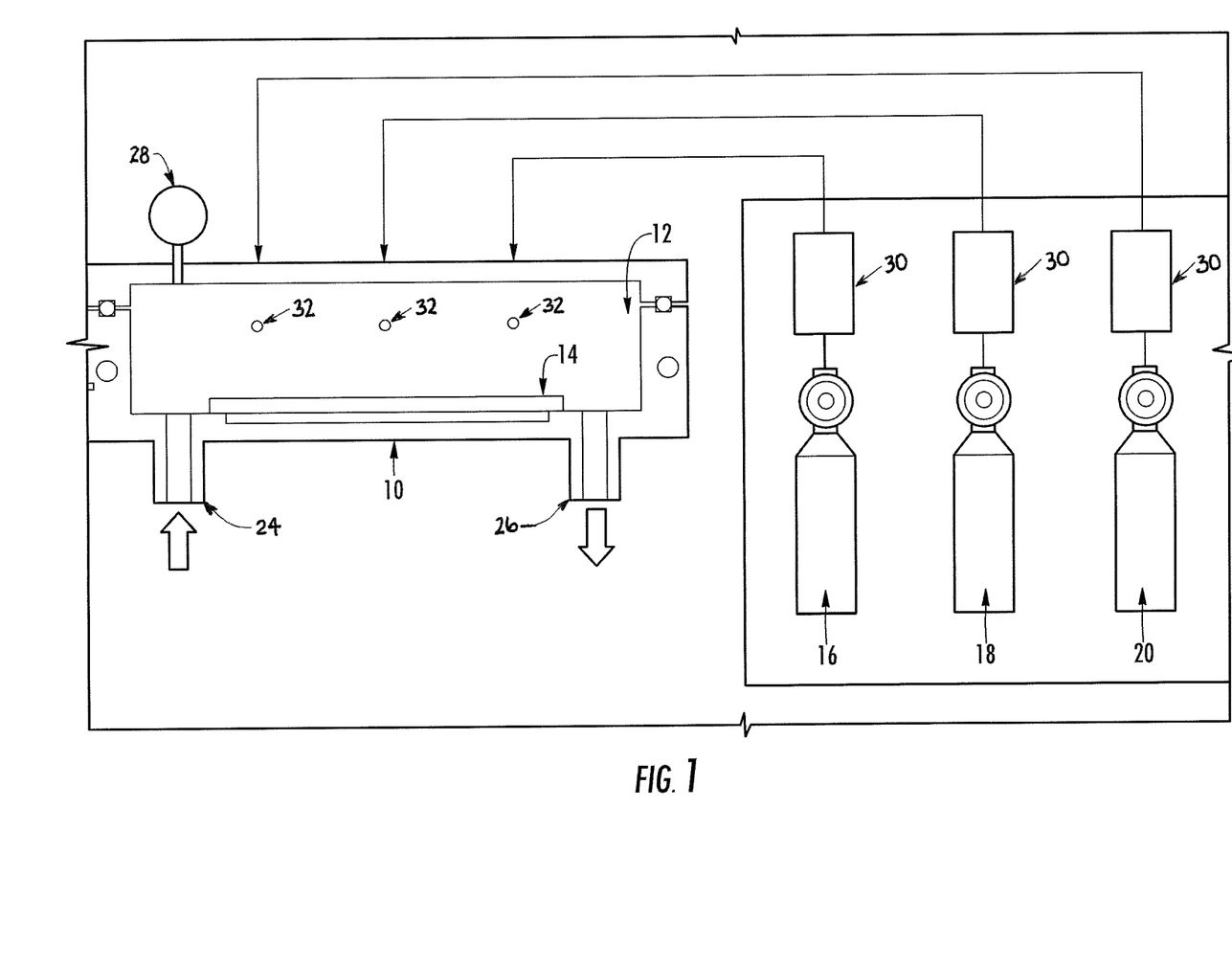
FIG. 1 is an overview of a molecular vapor deposition apparatus suitable for use in the present invention.

The method of preparing the surface of the medical implant is preferably performed using chemical vapor deposition/molecular vapor deposition. In one embodiment, a system such as that described in U.S. Patent Application Publication No. 2006/0251795, which is incorporated by reference herein, is used to apply a coating on the surface of the medical implant. The operation of a typical molecular vapor deposition system is shown in FIG. 1. The system 10 comprises a temperature-controlled vacuum coating chamber 12 in which the substrate 14 to be treated is held, and one or more storage vessels e.g., 16, 18, and 20, in fluid communication with the vacuum coating chamber containing liquid reagents that may be vaporized using vaporizers 30 prior to entering the coating chamber via injection ports 32. The liquid reagents may be, for example, precursors and/or catalysts. At the bottom of the figure, the upward arrow leading into the chamber 12 represents a plasma port 24, and the downward arrow extending outward from the chamber 12 represents a vacuum port 26. The pressure may be monitored via pressure gauge 28. The process may be utilized to produce thin, high quality, conformal coatings of almost any organic material with a boiling point below 150° C. The partial pressure of each vaporous component of the reactive mixture can be specifically controlled within the molecular vapor deposition system. The surface concentration and location of the reactive species deposited onto the substrate may be controlled by varying the total pressure in the processing chamber, the composition and number of the vaporous components, the partial pressure of each vaporous component, the temperature of both the substrate and the process chamber walls, and the reaction time. The thickness of the resulting coating layer on the substrate may be increased by performing multiple deposition cycles.

The substrate may be treated prior to being subjected to this process. For example, the surface of the substrate may be roughened, for example, by polishing with polishing paper, and/or air-abrading with alumina or other types of particles. The degree of surface roughening required may vary, depending on the particular application. In one embodiment, the surface is roughened with 50 micron alumina particles at 0.28 MPa for around 20 seconds, but these parameters may be varied as appropriate to achieve the desired result. The substrate may be treated with oxygen-containing plasmas to eliminate organic contaminants and to ensure surface hydroxylation.

Figure 2:
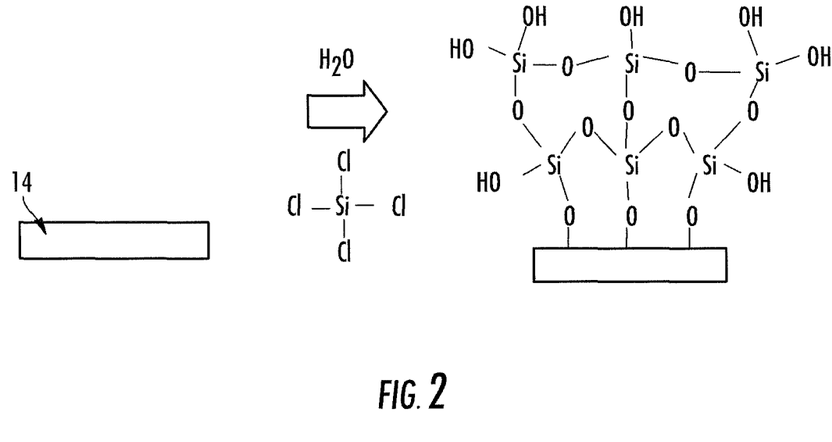
FIG. 2 is a schematic showing a chemical reaction representative of introducing water and silica tetrachloride to activate non-silica-based materials for subsequent silanation treatment.

In one embodiment of the invention, a silicon oxide coating is applied to the substrate. In such examples, the reagents utilized in the molecular vapor deposition include one or more silicon-based precursors. A schematic of the formation of a silicon oxide coating on a non-silica-based substrate 14 is presented in FIG. 2. In certain embodiments, substrate 14 may comprise, for example, a metal oxide surface such as $Al_2O_3$, $ZrO_2$, $TiO_2$ (on a Ti-based component), or $Cr_2O_3$ (on stainless steel or CoCr). As the silicon-based precursor and optionally one or more additional reagents react with the surface, active hydroxyl groups are formed on the surface, subsequently forming a silicon oxide layer on the substrate surface. The silicon-based precursor may be any silicon-containing species, including mono-, di-, and tri-silanes and siloxanes that can be vaporized. The silicon-based precursors include, but are not limited to, tetrachlorosilane ($SiCl_4$), tetrafluorosilane ($SiF_4$), tetrabromosilane ($SiBr_4$), trichlorosilane ($HSiCl_3$), trifluorosilane ($HSiF_3$), tribromosilane ($HSiBr_3$), hexachlorodisilane ($Si_2Cl_6$), hexachlorodisiloxane ($Si_2Cl_6O$), and combinations thereof. In one embodiment, the silicon-based precursor is tetrachlorosilane and an additional reagent is water vapor.

Although the reaction parameters can be adjusted, a typical tetrachlorosilane vapor pressure from a reservoir to be used for this reaction is about 18 torr; this vapor can be injected in the reaction chamber previously evacuated to a moderate vacuum (a few mtorr pressure). The partial pressure in the chamber after precursor injection can be anywhere between tenths of mtorr to a few torr, depending on the chamber volume in relation to the reservoir. Multiple injections (for example, 2 to 5) can be used to increase the amount of precursor in the chamber. The chamber can be kept at room temperature or a higher temperature (for example ranging from about 35 to about 50 degrees Celsius) to achieve more reproducible control over the reaction. Water vapor acting as a catalyst can be added to the reaction chamber after the precursor, with a typical partial pressure from the water reservoir ranging from about 8 to about 20 torr. Multiple injections (for example 2 to 5) can be used to increase the amount of water vapor in the chamber.

The thickness of the resulting layer may be varied by adjusting the reaction time and by adjusting the number of deposition cycles. In one embodiment, a medical implant is subjected to one or more 15 minute cycles. The resulting coating on the medical implant may range from less than about 1 nm to about 50 nm, from about 1 nm to about 25 nm, or from about 2 to about 15 nm. In the case of dental components treated with a silane coupling agent and bonded to another material, it has been determined that the silicon oxide layer thickness is preferably no more than about 25 nm, more preferably no more than about 15 nm, and most preferably no more than about 10 nm. In certain embodiments, the thickness is no more than about 5 nm in thickness or no more than about 3 nm in thickness. In some embodiments, multiple layers are deposited on the medical implant. The deposited silicon oxide layer may be continuous or discontinuous on the surface of the medical implant.

Figure 3A:
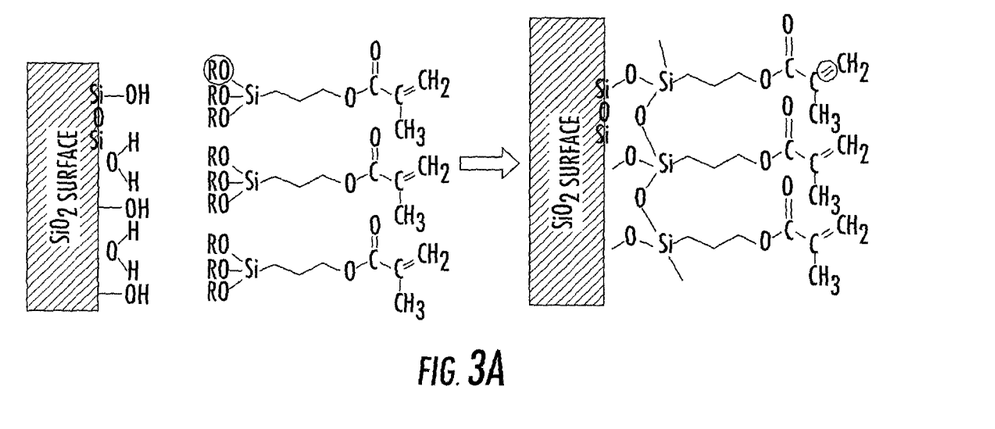
FIG. 3A is an illustration of silane coupling agents bonding to an inorganic surface such as silica.
Figure 3B:
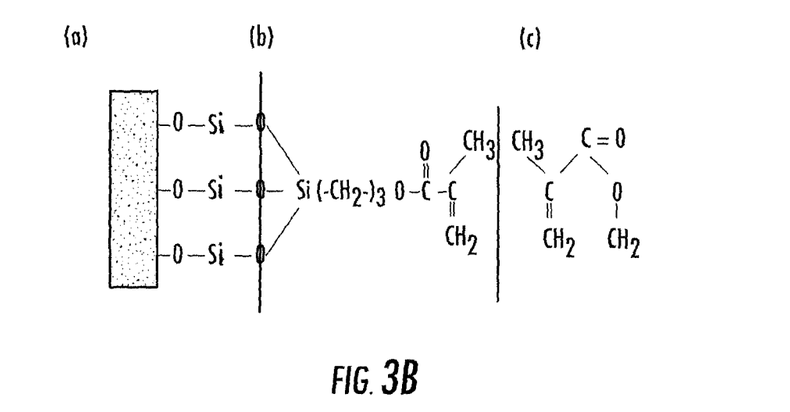
FIG. 3B is an illustration of silane coupling agents bonding to a high-strength ceramic material through molecular vapor deposition functionalization of the ceramic surface.

In another embodiment, the method further comprises applying a silane coupling agent to the coated medical implant. An illustration of how silanes typically bond to an inorganic surface such as silica is shown in FIGS. 3A and 3B. In FIG. 3A, the circle around the OR groups indicates that OR groups (e.g., $OCH_3$) may be hydrolyzed, becoming OH groups. In FIG. 3B, a) represents an MVD treated surface ($SiCl_4$), wherein the vertical block structure is a high strength ceramic, b) represents an attached organosilane, and c) represents a methacrylate polymer. By "silane" or "silane coupling agent" as used herein is meant any compound containing one or more silicon (Si) atoms. Silanes resemble orthoesters, and can be bifunctional. The silanes useful for the present invention are typically bifunctional with dual reactivity. In particular, they are typically able to react with an inorganic substrate and with an organic matrix. Such silanes may include one or more organic moieties, including but not limited to vinyl, allyl, amino, or isocyanato groups. They also typically contain one or more alkoxy groups (depicted in FIG. 3A as "RO" groups), including but not limited to methoxy and ethoxy groups. Silanes may contain one or more other substituents, which may be reactive, including chloride. There may also be an alkyl or alkylene link between the Si and the organic functionality Silanes may be hydrophilic or hydrophobic, and can also be anionic or cationic. In some embodiments, the silanes are trialkoxysilanes, with three alkoxy groups and one organic functionality. The silanes useful in the present invention include but are not limited to 3-methacryloyloxypropyltrimethoxysilane (3-trimethoxysilylpropylmethacrylate), 3-acryloyloxypropyltrimethoxysilane, 3-isocyanatopropyltriethoxysilane, N-[3-(trimethoxysilyl)propylethylenediamine], 3-mercaptopropyltrimethoxysilane, and bis-[3-(triethoxysilyl)propyl]polysulfide. There are many silanes that are commercially available. Examples include RelyX™ Ceramic Primer, Monobond™-S, Fusion,™ Vectris™ Wetting Agent, Porcelain Repair Primer, Pulpdent™ Silane Bond Enhancer, Silanator,™ Cerinate® Primer, Silicoup™ A and B, Ultradent™ Porcelain Etch & Silane, Clearfil™ Porcelain Bond Activator, Clearfil™ Ceramic Primer, Prolong Silane Bond Enhancer, Quadrant™ Porcelain Coupling Agent, Bifix DC,™ Bisco™ Porcelain Primer, Cimara,™ and ESPE™ Sil.™ Exemplary manufacturers of such silanes include 3M/ESPE, Ivoclar Vivadent, Pulpdent Corporation, Bisco, Inc., Kurayray, Premier Products Company, Mirage, Ultradent Products, Inc., George Taub Products, Cosmedent, VOCO America, Inc., Cavex Holland BV, and Kerr Corporation.

Applying a silane to an inorganic surface typically involves hydrolysis and condensation reactions with the surface. The silane may be applied in polar aqueous alcohol solutions, ethyl acetate, nonpolar solutions, or mixtures thereof. For example, the solution may comprise an acetone/ethanol mixture. Preferably, the silane is applied in aqueous alcohol solutions, such as 90-95% ethanol or isopropanol, or more dilute aqueous alcohol solutions from about 20-50% ethanol or isopropanol. FIG. 3A shows that the OR groups of the silane may be hydrolyzed, becoming OH groups. The one or more alkoxy groups and/or OH groups on the silane may react with free hydroxyl groups on the surface of the inorganic material. The silanes may react with other silanes to form dimers (siloxanes), which may condense to form siloxane oligomers. Such reactions may result in branched hydrophobic siloxane bonds. The siloxane oligomers, siloxane monomers, and/or silanes may react with the inorganic material to form M—O—Si bonds, wherein M is any metal. As used herein, M may refer to Si. In one embodiment, M is Si from the silicon dioxide coating that has been deposited on a substrate. In some embodiments, the substrate comprises a zirconia or alumina substrate which may be a medical implant. The film thickness of the silane layer is dependent on the concentration of the silane solution. The film may form a monolayer, but may be thicker, e.g., about 50-100 nm or more.

The organic functional end of the silane may be used to polymerize with an organic matrix such as a dental or orthopedic cement. Cement as used herein includes both traditional cements and resins, and refers to any adhesive material used to attach any synthetic or natural dental, orthodontic, or orthopedic implant or device to another substrate. Cements of particular interest herein are polymer-based cements, including methacrylate-based cements and include, but are not limited to, polymer-based adhesives, cements, and composites, and resin-modified glass ionomers. Exemplary dental cements which may be utilized in the present invention include, but are not limited to, the products identified by the tradenames Multilink® Universal Paste, Vivaglass® CEM, Appeal™ Esthetic Resin Cement, Variolink® Esthetic Resin Cement, Panavia,™ RelyX™ Unicem, RelyX™ Arc, Advance,™ Fuji Plus,™ Calibra,® Linkmax,™ Duolink,™

Integracem,™ Biscem,™ Imperva™ Dual, Contact Cure,™ Embrace,™ NX3 NEXUS® Cement, C&B Metabond,™ All-Bond,™ Geristore,® Vitique,® Permabond® Cyanloacrylate adhesive, and Superbond C&B.™ Exemplary manufacturers of such dental cements include, but are not limited to, Ivoclar Vivadent, Kuraray, Bisco, Inc., Kerr Corporation, Premier Products Company, Pulpdent Corporation, 3M/ESPE, Cosmedent, Dentsply International, GC America Inc., Parkell Inc., and Ultradent Products Inc.

The type of cement chosen may depend on the structure to which the medical implant is to be bonded. For example, a glass ionomer or zinc polycarboxylate cement is typically used to attach an implant or restorative to natural tooth. Other considerations in the selection of a dental cement include solubility, erosion, tensile strength, shear strength, toughness, elastic modulus, creep, working and setting time, sensitivity to moisture during and after setting, thermal conductivity and diffusivity, pH during setting, biocompatibility, compatibility with other restorative materials, potential for fluoride release, adhesion to enamel and dentine, sensitivity of setting reaction to temperature, rate of change in viscosity, film thickness, and dimensional change in the presence of moisture. Glass ionomer cements are capable of releasing fluoride, and may be particularly suitable in geriatric dentistry. The resin and resin-glass ionomer cements are stronger and tougher than the other cements. In one embodiment of the present invention, a resin-based cement is used.

The cements may contain various other additives. Some cements include ingredients to etch, prime, and/or bond. Some cements include components that are capable of releasing fluoride on a sustained basis. Cements may or may not be adhesive. For example, zinc phosphates are typically not adhesive, while resin-modified glass ionomers exhibit both chemical and mechanical adhesion.

The cements may be temporary or permanent, but preferably are permanent. The cement may be applied to the silane functionalized surface of the medical implant by any means known in the art. Cements are often sold as powders and are mixed with liquid prior to use and applied to the organo-functionalized silane surface and to the material to which the medical implant will be coupled. Variables affecting the cement and the success of the bonds formed include mixing time, humidity, powder to liquid ratio, and temperature. Alternatively, the cement may be sold and used as a paste. Some cements, such as polymer-based resins, require curing. Curing typically requires the use of light or chemical activation or may require both. Alternatively, some cements are self-curing.

The coated medical implant may be attached to various types of material using the cement. In some embodiments, the coated medical implant is a dental component, which may be bonded, for example, to any underlying substrate (e.g. tooth structure or implanted abutment). In other embodiments, the cement may be used to bond the coated medical implant to a ceramic, porcelain or metal material. In one embodiment, the coated medical implant is a dental implant, which is attached to a crown that may comprise any material, including a metal, porcelain fused to metal, porcelain, ceramic, or resin.

Another embodiment provides a medical implant that is coated according to the processes described above. The medical implant is preferably zirconia or alumina but may comprise any material which may have available hydroxyl groups on its surface. The implant may be coated using molecular vapor deposition to provide a functionalized surface. In one embodiment, the implant is coated with a silicon oxide layer using molecular vapor deposition. The coating may be full or partial. The coating may be continuous or discontinuous. In one embodiment, the coating is full, meaning that the surface of the medical implant is completely coated. The thickness of the coating may vary.

In some embodiments, the silicon oxide coating is chemically attached or chemisorbed to the medical implant. By chemically attached or chemisorbed is meant that there exists a chemical bond between the silicon oxide coating and the surface of the medical implant. The bond may be of any strength and type, but is preferably a strong covalent bond. In some embodiments wherein multiple layers of silicon dioxide are deposited, the additional layers may be physisorbed onto adjacent layers rather than chemisorbed.

The silicon oxide coating on the medical implant may be further functionalized with a silane coupling agent as described above to give a medical implant with an organic-functionalized surface. A cement may be reacted with the silane coupling agent to give a medical implant coated with cement, which may be subsequently affixed to a variety of surfaces. In one embodiment, the cement is covalently bonded to the silane coupling agent. In one embodiment, the medical implant is a dental component that may be affixed using the cement to any natural or synthetic dental component or substrate.

Although the description and examples focus on dental components as an example of medical implants, the methods and compositions of the invention may also be applicable to other types of medical implants. For example, orthopedic implants such as replacement joints that are affixed by a cement may be treated according to the methods of the present invention.

EXPERIMENTAL

Example 1

Preparation of Samples

Blocks of pre-sintered zirconia and porcelain (ZirCAD® and ProCad,® Ivoclar Vivadent, Schaan, Liechtenstein) measuring 14×12×20 mm were obtained from the manufacturers. Composite blocks (AELITE™ All-Purpose Body, Bisco, Inc., Schaumburg, Ill.) were fabricated by condensing the material into a Teflon® mold (14×12×20 mm) in 2 mm increments, light curing each increment for 40 seconds at 500 mW/cm$^2$. Surfaces of each material were polished through 1200-grit abrasive paper to ensure uniform starting surface roughness. After polishing, the surfaces were air-abraded (50 µm alumina abrasive, 0.29 MPa, 20 sec) prior to chemical surface treatments or bonding procedures. Specimens were placed in an ultrasonic DI bath for 5 minutes.

The zirconia surface functionalization was performed using SiCl$_4$ (Gelest SIT7085.0, Gelest, Inc., Morrisville, Pa.) by vapor deposition in a commercial tool (MVD-100, Applied Microstructures, San Jose, Calif.). The samples were exposed for 14 minute cycles to a controlled amount of vapor from a liquid SiCl$_4$ precursor together with controlled amount of water vapor acting as a catalyst. SiCl$_4$ depositions were pre-calibrated by deposition on silicon wafers followed by measurement of the Si$_x$O$_y$ seed layer thickness via ellipsometry. Two film thicknesses were used for this study: 2.6 nm and 23 nm and they were obtained by increasing the number of deposition cycles. After the zirconia specimens were cleaned, they were placed in the chemical vapor deposition/molecular vapor deposition instrument. Prior to deposition, the surfaces were exposed to 10-minute oxygen plasma, which cleans any organic contaminants and ensures surface hydroxylation. For a detailed description of the procedure, see Kobrin et al, Durable Anti-Stiction Coatings by Molecular Vapor Deposition (MVD), *NSTI Nanotech* 2005; 2: 247-350, incorporated herein by reference.

Example 2

Microtensile Tests

The following different types of specimens were prepared for mirotensile tests.

1) Porcelain was acid-etched using 9.5% HF gel (Porcelain Etchant, Bisco, Inc., Schaumburg, Ill.) for 60 seconds, rinsed and dried, and treated with silane (Porcelain Primer, Bisco, Inc., Schaumburg, Ill.). Resin adhesive was brushed onto both the porcelain and composite mating surfaces (air dried and light cured for 10 seconds). The porcelain and composite blocks were bonded together using a resin luting cement (C&B Cement, Bisco, Inc., Schaumburg, Ill.) under a fixed load of 20N.

2) Zirconia (no surface treatment) was treated with silane and bonded to composite blocks (unless otherwise noted, all adhesive materials were the same for all groups).

3) Zirconia (no surface treatment) was silica-coated using 30 μm alumina particles modified with salicylic acid (Co-Jet,™ 3M™-ESPE,™ St. Paul, Minn. −0.28 MPa, 5-10 nm working distance, 15 sec), treated with silane, and bonded to composite blocks.

4) Zirconia ($Si_xO_y$ seed layer deposited by molecular vapor deposition, with thickness of approximately 2.6 nm) was treated with silane and bonded to composite blocks.

5) Zirconia ($Si_xO_y$ seed layer deposited by molecular vapor deposition, with thickness of approximately 23 nm silica layer) was treated with silane and bonded to composite blocks.

6) Composite bars were constructed and tested to calculate the inert bond strength.

After storage at room temperature for a period of 24 hours, the bulk specimens were cut into plates using a low-speed diamond-coated saw (Isomet 1000, Buehler, Lake Bluff, Ill.). The plates were then subsequently cut into bars (approximately 1.5 mm×1.5 mm) using a high precision cutting saw (DAD 341, Disco Corp., Tokyo, Japan). Specimens were then attached to a microtensile fixture with cyanoacrylate adhesive (Permabond,® Pottstown, Pa.). All specimens were subjected to a tensile force at a crosshead speed of 1 mm/min in an EZ-Test testing device (Shimadzu, Kyoto, Japan). Bond strengths were calculated by dividing fracture peak load by the cross-sectional area of the specimen. Single-factor analysis of variance (ANOVA) at a 5% confidence level was performed for the bonding strength data.

Figure 4:
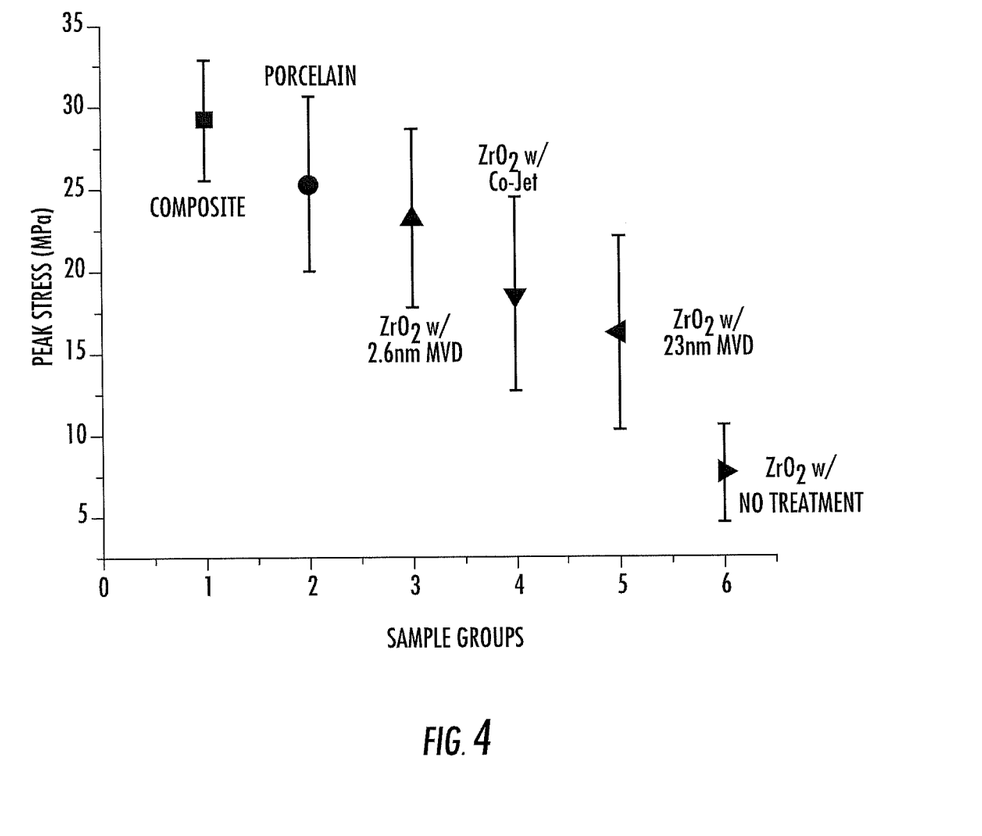
FIG. 4 is a graph showing microtensile testing peak stress values for all substrate materials tested, plotted with standard deviation error bars.

Mechanical data obtained for the strength testing of each group is shown in FIG. 4, with the mean strength value and standard deviation of the data for each group. ANOVA revealed a significant difference in mean microtensile bond strengths. Composite microtensile bars were fabricated to create a control strength value (29.2 MPa) and used to gauge the measured mean strength values of tested groups. The untreated zirconia specimens had the lowest strength values and were the only group to show failure during cutting. The samples with surface treatments exhibited higher bond strengths and none of them failed during cutting. These had the highest percentage of composite failure where the failure mode is within the composite and not the bonding interface, which has been determined to be clinically the most desirable failure mode.

The zirconia sample with a 2.6 nm silicon oxide layer deposited by molecular vapor deposition (group 3) shows similar peak stress as porcelain and composite materials, and statistically has the same bond strength as the bonded porcelain specimens. Approximately 85% of the failures for both groups were shown to be mixed mode (adhesive/cohesive) or cohesive failure. The group 3 zirconia sample displayed higher mean strength than the current systems used clinically for adhering zirconia to dental materials (groups 4 and 6—zirconia with Co-Jet™ treatment or with no treatment). Group 3 is also stronger than the zirconia with a thicker silicon oxide layer prepared via the same method, suggesting that the bond strength for these samples is a function of treatment thickness. It is possible that the thicker seed layers have a level of chemisorbed $Si_xO_y$ near the zirconia surface with stacking of additional layers being physisorbed. These additional layers that are not chemically linked provide reduced bonding to silane hydrocarbons. The zirconia sample with the 23 nm silicon oxide layer deposited by molecular vapor deposition (group 5) shows similar strength to the untreated zirconia surface (group 6). Because the specimens prepared via a tribochemical technique (group 4) had higher bond strengths than the untreated control (group 6), but lower than the best silica seed layer-treated surface (group 3), there may be a benefit from both roughening and chemical functionalization of the surface.

Peak stress values from samples with surface treatment have higher standard deviation than the controls because of variations in failure modes. These groups included cases of cohesive failure (highest bond strength) and combinations of cohesive and adhesive failure, which created a large spread in bond strength values. Values for peak stress with standard deviations and percent breakdown of failure mode are shown in Table 1 below.

TABLE 1

Microtensile Peak Stress (MPa) with standard deviation of the different test groups (numbers of specific failure types are represented in percentages).

| Group | Peak Stress (SD) (MPa) | Adhesive (%) | Mixed (%) | Cohesive (%) |
|---|---|---|---|---|
| Composite (bars only) | 29.2 (3.7) | | Control | |
| Porcelain (control) | 25.3 (5.3) | 16 | 35 | 49 |
| Zirconia ($Si_xO_y$-treated, 2.6 nm thickness) | 23.2 (5.4) | 15 | 40 | 45 |
| Zirconia (Co-Jet ™ treatment) | 18.6 (5.9) | 32 | 52 | 16 |
| Zirconia ($Si_xO_y$-treated, 23 nm thickness) | 16.2 (5.9) | 50 | 43 | 7 |
| Zirconia (no treatment) | 7.6 (3.0) | 72 | 28 | — |

Example 3

Determination of Failure Mode by SEM

Figure 5A:
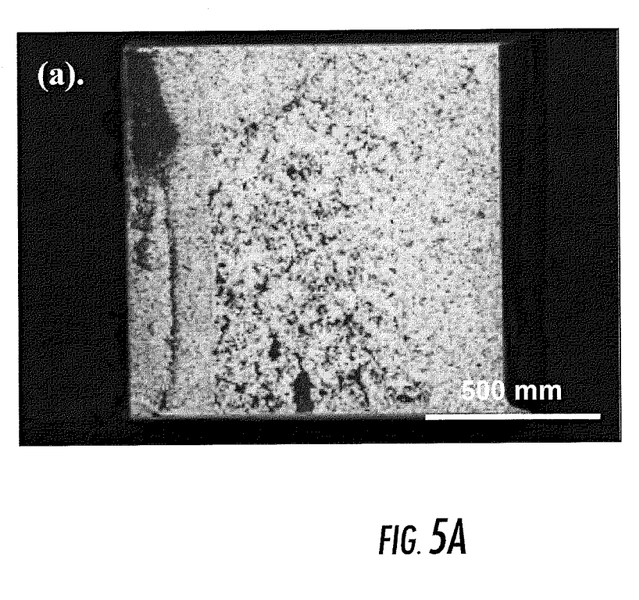
FIGS. 5A and 5B are SEM micrographs of zirconia without surface treatment, wherein the white areas are the zirconia surface and the dark regions are areas of resin cement.
Figure 5B:
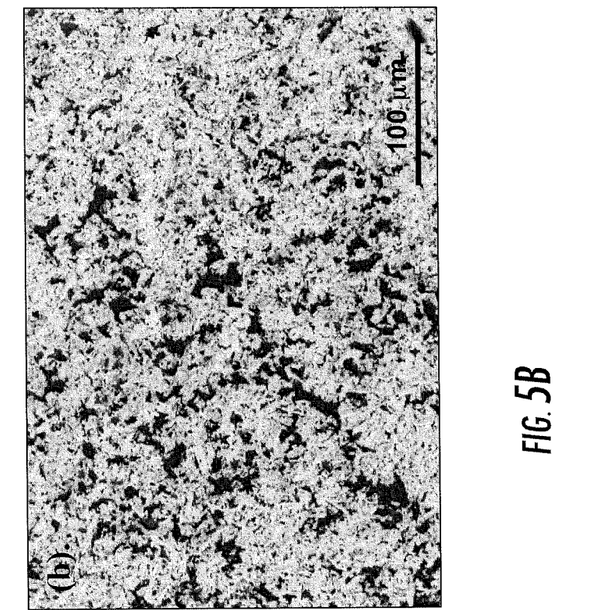
Figure 6A:
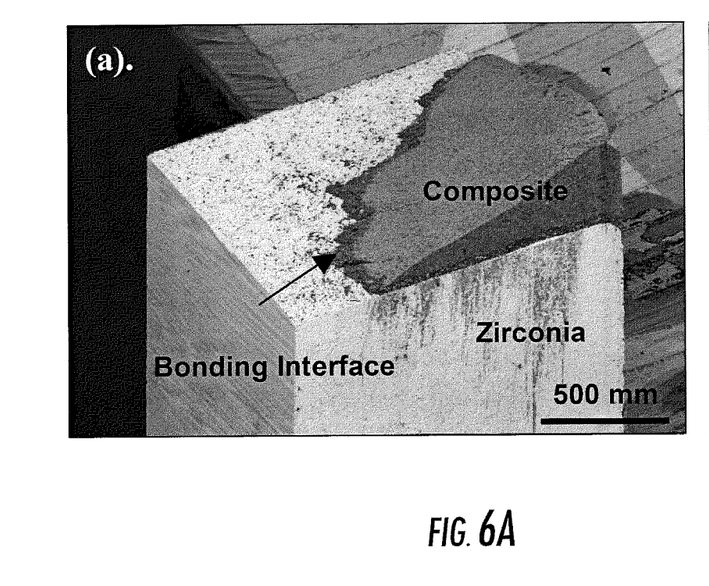
FIGS. 6A and 6B are SEM micrographs of zirconia with a 23 nm silica seed layer-treated surface.
Figure 6B:
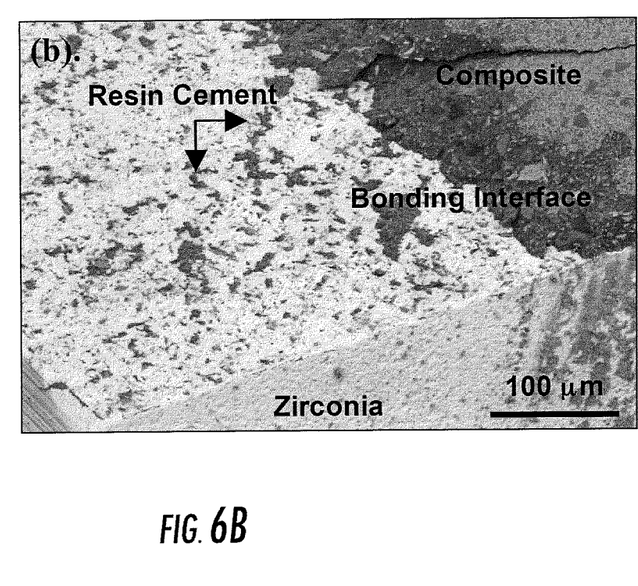
Figure 7A:
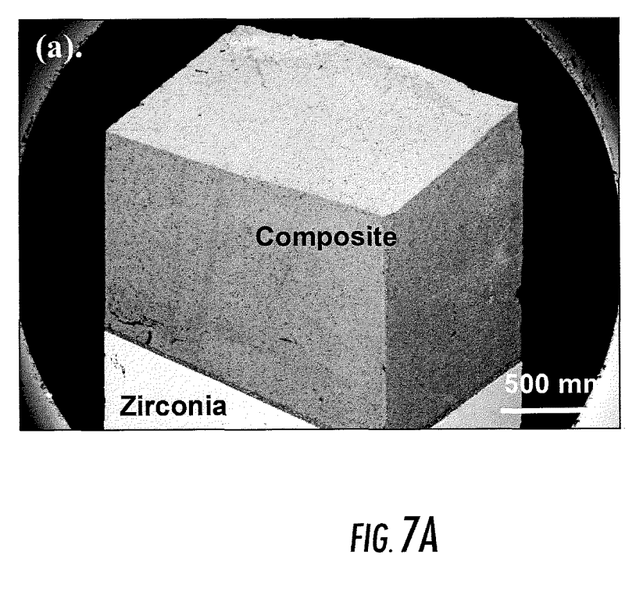
FIGS. 7A and 7B are SEM micrographs of a 2.3 nm silica seed layer-treated surface.
Figure 7B:
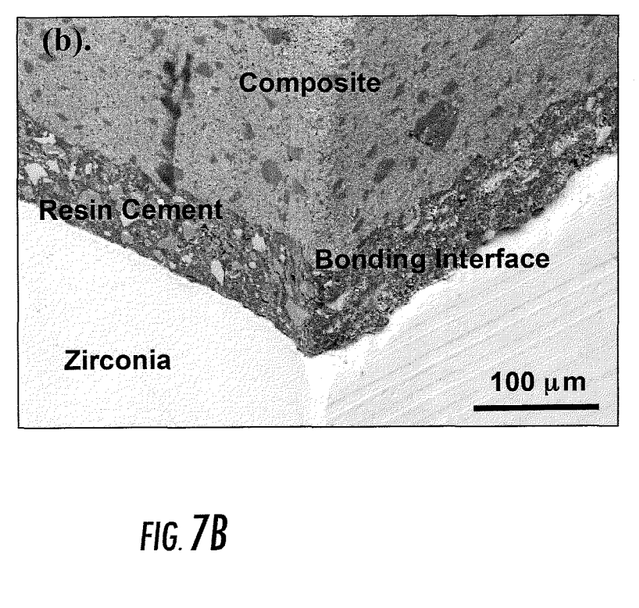

Scanning Electron Microscopy (SEM) was used to evaluate the mating surfaces of the fractured specimens to determine failure mode, either composite cohesive failure (partial or complete cohesive failure within the composite) or adhesive failure (partial or complete adhesive failure). SEM analysis of the fractured microtensile bars revealed several types of failure modes: (1) adhesive failure, (2) mixed mode of adhesive and cohesive failure, and (3) cohesive failure. FIGS. 5A and 5B illustrate a typical adhesive failure where the bond interfacial surfaces are exposed, represented at two different magnifications. Here, the zirconia surface can be discerned, with areas of resin cement. FIGS. 6A and 6B and FIGS. 7A and 7B illustrate two further different failure modes, respectively, a mixed mode (failure surface displays areas of exposed bonding surface and remnants of composite failure) and cohesive failure (wherein the fracture is purely in the composite). Again, each of these figures includes images at two different magnifications.

The SEM results confirm that the majority of the specimen failures had remaining composite material still adhered to the zirconia. This data suggests a benefit from both roughening and chemical functionalization of the surface.

Example 4

XPS Analysis of Surface Composition

Several samples (porcelain, alumina, and zirconia) were analyzed using X-Ray Photoelectron Spectroscopy (XPS). This method is widely used to evaluate the chemical composition of a surface. The analysis is done by irradiating a sample with soft x-rays to ionize atoms and releasing core-level photoelectrons. The kinetic energy of the escaping photoelectrons limits the depth from which it can emerge, giving XPS its high surface sensitivity and sampling depth of a few nanometers. Photoelectrons are collected and analyzed by the instrument to produce a spectrum of emission intensity versus electron binding energy. Since each element has a unique set of binding energies, XPS can be used to identify the elements on the surface. Also, peak areas at nominal binding energies can be used to quantify concentration of the elements.

Figure 8:
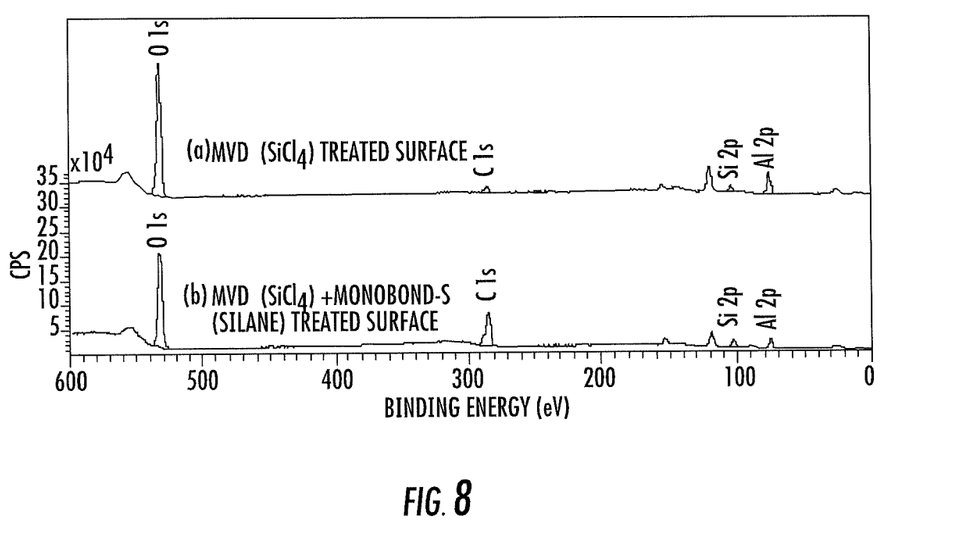
FIG. 8 is a representative XPS survey scan of an alumina sample treated via a molecular vapor deposition process and via the application of Monobond™ (a commercial dental organo-silane) on the treated surface.

A baseline of each sample was analyzed, being an untreated, native surface. Each sample was then treated with Monobond™ (Ivoclar Vivadent, Schann, Liechtenstein) organo-silane coupling agent. Monobond™ contains 3-methacryl-oxypropyltrimethoxy-silane (MPS) as the effective silane (~1% in weight) in a solution of ethanol (~52% in weight) and distilled water (~47% in weight), and has a pH of 4 (Matinlinna et al., An Introduction to Silanes and their Clinical Applications in Dentistry, *Int. J. Prosthod.* 2004, 17: 155-164). XPS results showed no signs of silanation on native surfaces for both the alumina and zirconia, which was expected based on previous reports (Blatz et al., Resin-Ceramic Bonding: A Review of the Literature, *J. Prosthet. Dent.* 2003, 89: 268-274, and Kern & Wegner, Bonding to Zirconia Ceramic: Adhesion Methods and their Durability, *Dent. Mat.* 1998, 14: 64-71). The alumina and zirconia were then exposed to the molecular vapor deposition process to create a Si-based "seed" layer. The recipe for the $SiCl_4$ was calibrated to deposit approximately 1.7 nm. Due to the reaction, it was anticipated that a monolayer of Si would be bonded to the oxide surface. FIG. 8 is a representative XPS survey scan of an alumina sample treated via molecular vapor deposition and application of Monobond™ on the treated surface. There are several interesting conclusions that can be made by analyzing the scans: (1) there exists approximately a monolayer of Si at the surface and (2) the level of C is increased after the application of Monobond,™ which would be expected due to the tethering of the hydrocarbons. It should be noted that the zirconia sample displayed similar results as the reported alumina sample, leading to the conclusion that a zirconia surface can be altered in a similar fashion. Table 2 displays the relative atomic percentages as calculated from XPS scans of both zirconia and alumina treated samples. Additionally, samples were kept in atmospheric conditions for a period of 2 weeks and XPS data displayed no bonding degradation.

TABLE 2

Elemental atomic percentages as calculated from XPS surface scans of treated zirconia and alumina samples.

|  | O | C | Si | Zr |
|---|---|---|---|---|
| Zirconia |  |  |  |  |
| $Si_xO_y$-treated | 54.28 | 8.00 | 7.94 | 29.78 |
| $Si_xO_y$-treated/MB | 40.65 | 35.61 | 8.11 | 15.63 |
| Alumina |  |  |  |  |
| $Si_xO_y$-treated | 56.57 | 7.40 | 6.11 | 29.92 |
| $Si_xO_y$-treated/MB | 40.00 | 38.81 | 6.15 | 15.05 |

$Si_xO_y$-treated = surface functionalized via molecular vapor deposition
MB = further coupled to Monobond ™-S
Note:
values are in calculated atomic %.

Figure 9:
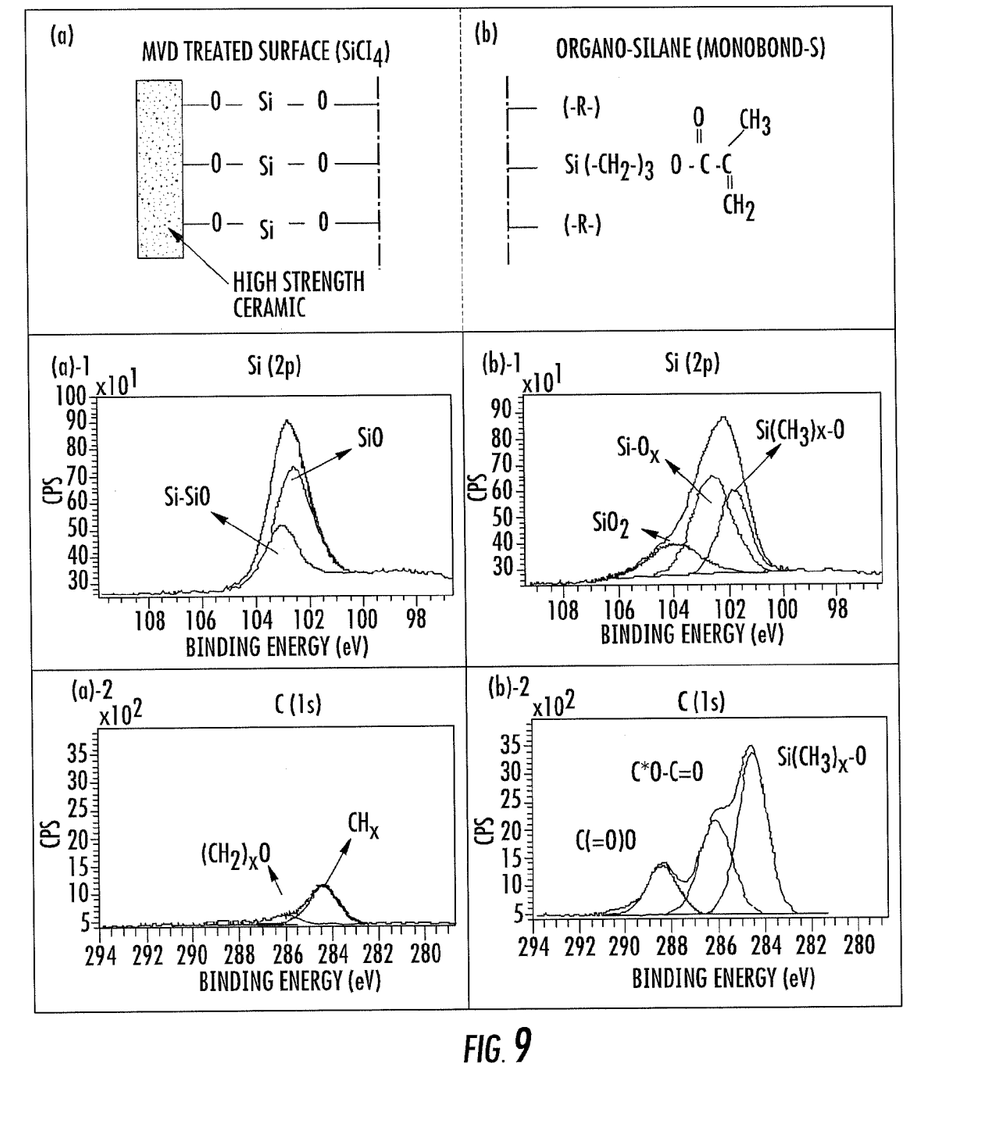
FIG. 9 is a comparison of the expected surfaces of a silicon oxide-treated alumina surface prepared using molecular vapor deposition and a silicon oxide-treated alumina surface prepared using molecular vapor deposition coupled to Monobond™ (a commercial dental organo-silane) and XPS high resolution core scans of the surfaces.

Representative survey scans of a $Si_xO_y$-treated alumina surface prepared via molecular vapor deposition and a $Si_xO_y$-treated alumina surface prepared via molecular vapor deposition further coupled to Monobond™-S are shown in FIG. 9. Illustrated in (a) and (b) is the expected chemical bonding structure of (a) a surface treated with the MVD treatment ($SiCl_4$) and (b) a surface with MVD treatment and application of an organosilane (Monobond™-S). Subsequent XPS high resolution core scans (FIGS. 9(a)-1 through (b)-2) were performed to evaluate each peak. These core scans identify specific bonding structures for both the Si(2p) and C(1s) that are critical in describing the ability to alter a surface for efficient silanation. The addition of Monobond™-S to the surface broadens the Si(2p) peak with a shift of the peak maximum to a lower BE by approximately –0.5 eV. Silicon from the Monobond™-S addition (FIG. 9(b)-1) has a lower binding energy because one of its neighbors is a hydrocarbon chain (Si—$(CH_3)_x$—O), which draws less electron density from Si than an oxygen neighbor (Si—O). Although the population of Si has increased, the emitted photoelectrons are partially attenuated by the long hydrocarbon chain between Si and the XPS detector path. Also note that the shoulder on the higher energy side coincides with the original molecular vapor deposition peak. Since this peak area is further attenuated than Si from Monobond™-S but is close to half of the peak area, the relative concentrations must be similar for the $Si_xO_y$-treated alumina surface and the $Si_xO_y$-treated alumina surface further coupled to Monobond™-S and thus each is likely to be a monolayer. The C(1s) spectra show that adventitious carbon peaks for the $Si_xO_y$-treated alumina surface (FIG. 9(a)-2) are from atmospheric contaminants. The core level scan for the $Si_xO_y$-treated alumina surface further coupled to Monobond™-S (FIG. 9(b)-2) shows successful addition of Monobond™-S to the $Si_xO_y$-treated alumina surface. The relative amounts and characteristic chemical shifts are evident with the Si—$(CH_3)_x$—O, C*O—C═O, and C(═O)O, which is what is expected based on the chemical structure of Monobond™-S. The total C(1s) was approximately 39% of the survey scan, which was also indicative of a monolayer of Monobond™-S based on the expected attenuation from the molecular structure of Monobond™-S.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A medical implant constructed of refractory metal oxide and having a surface and a silicon oxide coating layer chemisorbed on said surface, wherein the silicon oxide layer is deposited by chemical vapor deposition, and wherein the refractory metal oxide comprises zirconia.

2. The medical implant of claim 1, wherein the medical implant is a dental component selected from the group consisting of dental implants, crowns, bridges, fillings, veneers, inlays, onlays, endodontic devices, and orthodontic brackets.

3. The medical implant of claim 1, wherein the medical implant is a dental component, and further comprising a silane coupling agent covalently attached to the silicon oxide layer.

4. The medical implant of claim 3, wherein the silane coupling agent is a selected from the group consisting of 3-methacryloyloxypropyltrimethoxysilane, (3-trimethoxysilylpropylmethacrylate), 3-acryloyloxypropyltrimethoxysilane, 3-isocyanatopropyltriethoxysilane, N-[3-(trimethoxysilyl)propylethylenediamine], 3-mercaptopropyltrimethoxysilane, bis-[3-(triethoxysilyl)propyl]polysulfide, and combinations thereof.

5. The medical implant of claim 3, further comprising an overlying dental cement coupled to the silane coupling agent.

6. The medical implant of claim 5, wherein the dental cement is selected from the group consisting of polymer-based adhesives, cements, resin-modified glass ionomers, and combinations thereof.

7. The medical implant of claim 5, wherein the cement is covalently bonded to the silane coupling agent.

8. The medical implant of claim 1, wherein the thickness of the silicon oxide layer is between about 0.1 and about 50 nm.

9. The medical implant of claim 1, wherein the thickness of the silicon oxide layer is less than about 30 nm.

10. The medical implant of claim 1, wherein the thickness of the silicon oxide layer is less than about 10 nm.

11. A dental structure, comprising:
a first dental component constructed of a refractory metal oxide and having a surface, wherein the refractory metal oxide comprises zirconia;
a silicon oxide coating layer chemisorbed on the surface, wherein the silicon oxide layer is deposited by chemical vapor deposition;
a silane coupling agent overlying and covalently attached to the silicon oxide layer;
a dental cement overlying and coupled to the silane coupling agent; and
a second dental component having a surface bonded to the dental cement.

12. The dental structure of claim 11, wherein one of the first and second dental components is selected from the group consisting of dental implants, crowns, bridges, fillings, veneers, inlays, onlays, endodontic devices, and orthodontic brackets.

13. The dental structure of claim 11, wherein the silane coupling agent is a selected from the group consisting of 3-methacryloyloxypropyltrimethoxysilane, (3-trimethoxysilylpropylmethacrylate), 3-acryloyloxypropyltrimethoxysilane, 3-isocyanatopropyltriethoxysilane, N-[3-(trimethoxysilyl)propylethylenediamine], 3-mercaptopropyltrimethoxysilane, bis-[3-(triethoxysilyl)propyl]polysulfide, and combinations thereof.

14. The dental structure of claim 11, wherein the dental cement is selected from the group consisting of polymer-based adhesives, cements, resin-modified glass ionomers, and combinations thereof.

15. The dental structure of claim 11, wherein the thickness of the silicon oxide layer is between about 0.1 and about 50 nm.

16. The dental structure of claim 11, wherein the thickness of the silicon oxide layer is less than about 30 nm.

17. The dental structure of claim 11, wherein the thickness of the silicon oxide layer is less than about 10 nm.

18. The dental structure of claim 11, wherein the surface of the second dental component is constructed of a material selected from the group consisting of natural tooth, metal, porcelain fused to metal, porcelain, ceramic, resin, and combinations thereof.

19. A method of preparing the surface of a medical implant for silanation, comprising:
providing a medical implant constructed of refractory metal oxide comprising zirconia; and
applying a silicon oxide coating layer to the surface of the medical implant by chemical vapor deposition.

20. The method of claim 19, wherein the application step comprises contacting the surface with one or more gaseous silicon-based precursors and water vapor.

21. The method of claim 20, wherein the silicon-based precursor is selected from the group consisting of tetrachlorosilane ($SiCl_4$), tetrafluorosilane ($SiF_4$), tetrabromosilane ($SiBr_4$), trichlorosilane ($HSiCl_3$), trifluorosilane ($HSiF_3$), tribromosilane ($HSiBr_3$), hexachlorodisilane ($Si_2Cl_6$), hexachlorodisiloxane ($Si_2Cl_6O$), and combinations thereof.

22. The method of claim 19, wherein the medical implant is a dental component and the method further comprises reacting the silicon oxide coating layer of the dental component with a silane coupling agent.

23. The method of claim 22, wherein the silane coupling agent is selected from the group consisting of 3-methacryloyloxypropyltrimethoxysilane, (3-trimethoxysilylpropylmethacrylate), 3-acryloyloxypropyltrimethoxysilane, 3-isocyanatopropyltriethoxysilane, N-[3-(trimethoxysilyl)propylethylenediamine], 3-mercaptopropyltrimethoxysilane, bis-[3-(triethoxysilyl)propyl]polysulfide, and combinations thereof.

24. The method of claim 22, further comprising coupling the silane coupling agent to a dental cement.

25. The method of claim 24, wherein the dental cement is selected from the group consisting of polymer-based adhesives, cements, resin-modified glass ionomers, and combinations thereof.

26. The method of claim 24, further comprising bonding the dental component to another substrate with the dental cement.

27. The method of claim 19, wherein the thickness of the silicon oxide coating layer introduced in the applying step is less than about 10 nm.

28. The method of claim 19, wherein the thickness of the silicon oxide coating layer introduced in the applying step is less than about 30 nm.

29. The method of claim 19, wherein the method further comprises roughening the substrate surface prior to said applying step.

30. The method of claim 19, wherein the method further comprises treating the substrate surface with oxygen-containing plasma prior to said applying step.

* * * * *